United States Patent [19]

Shibano et al.

[11] Patent Number: 4,625,059

[45] Date of Patent: Nov. 25, 1986

[54] PROCESS FOR PURIFICATION OF 1,2-UNSATURATED CARBOXYLIC ACIDS AND/OR ESTERS THEREOF

[75] Inventors: Takeshi Shibano; Yasuyuki Sakakura; Kiichi Ito; Kazuhiko Higuchi, all of Yokkaichi, Japan

[73] Assignee: 501 Mitsubishi Petrochemical Company, Ltd., Tokyo, Japan

[21] Appl. No.: 623,772

[22] Filed: Jun. 22, 1984

[30] Foreign Application Priority Data

Jun. 24, 1983 [JP] Japan ................................ 58-112646

[51] Int. Cl.$^4$ .............................................. C07C 51/48
[52] U.S. Cl. .................................... 562/600; 562/532; 562/534; 562/535; 562/545; 562/546; 562/547; 560/218
[58] Field of Search ................ 562/600, 532, 534–535, 562/545–547; 560/218

[56] References Cited

U.S. PATENT DOCUMENTS 3,725,208 4/1973 Maezawa et al. .................... 562/600
3,893,895 7/1975 Dehnert et al. ......................... 203/59

FOREIGN PATENT DOCUMENTS 88143 6/1982 Japan .................................... 562/600

*Primary Examiner*—Werren B. Lone
*Attorney, Agent, or Firm*—Robert E. Burns; Emmanuel J. Lobato; Bruce L. Adams

[57] ABSTRACT

A 1,2-unsaturated carboxylic acid or its ester such as acrylic or methacrylic acid or its alkyl ester is purified to remove aldehyde impurities contained therein by treating the acid or its ester with a mercapto containing compound in the presence of an acid catalyst.

9 Claims, No Drawings

PROCESS FOR PURIFICATION OF 1,2-UNSATURATED CARBOXYLIC ACIDS AND/OR ESTERS THEREOF

BACKGROUND OF THE INVENTION

1. Field of the Invention

This invention relates to a process for purifying a 1,2-unsaturated carboxylic acid (otherwise known as an alpha, beta-unsaturated carboxylic acid or a 2-unsaturated carboxylic acid) and/or its esters.

In accordance with the process of the present invention, aldehydes contained as impurities in 1,2-unsaturated carboxylic acids and/or their esters can be removed efficiently by simple operations.

2. Prior Art 1,2-Unsaturated carboxylic acids such as acrylic acid, methacrylic acid, etc. and/or their esters have a broad range of uses as starting materials for synthesis of high-molecular compounds.

These 1,2-unsaturated carboxylic acids have been produced industrially through a vapor-phase catalytic oxidation reaction of alkenes and/or alkenals, etc., in recent years. However, the 1,2-unsaturated carboxylic acids such as acrylic acid and methacrylic acid produced according to the above method contain various types of impurities such as aldehydes, e.g., formaldehyde, acetaldehyde, propionaldehyde, isobutylaldehyde, acrolein, methacrolein, furfural, and benzaldehyde; ketones, e.g., acetone; or acids, e.g., formic acid, acetic acid, and propionic acid.

A considerable amount of these impurities are separated and removed by repeating conventional purification methods such as distillation, extraction and the like.

However, aldehyde impurities remain in the 1,2-unsaturated carboxylic acids, because (i) aldehydes are newly formed during the above mentioned purification operations such as distillation and extraction (for example, acrolein contained in acrylic acid is thermally converted to acrolein dimer during the purification process of the acrylic acid) and (ii) aldehydes such as furfural and benzaldehyde have boiling points close to that of acrylic acid and separation thereof from the acrylic acid by distillation operation is difficult.

On the other hand, in the industrial production of 1,2-unsaturated carboxylic acid esters, these esters are usually obtained by esterification of the corresponding 1,2-unsaturated carboxylic acids which have been produced at a low cost according to the above-mentioned industrial method and purification by simple distillation. Thus, the resulting 1,2-unsaturated carboxylic acid esters are inevitably contaminated with aldehyde impurities as mentioned above.

When such 1,2-unsaturated carboxylic acids and/or their esters containing the aldehyde impurities are used as starting materials for synthesis of high-molecular compounds, these impurities cause various problems such as a polymerization-inhibition effect and coloring of the resulting polymers.

Examples of methods for removing aldehyde impurities contained in 1,2-unsaturated carboxylic acids and/or their esters are a distillation method; an adsorption method using activated carbon or molecular sieves having an amine compound adsorbed thereon (Japanese Laid-Open Patent Specification No. 18934/81); and a method of forming sulfite-addition products by the addition reaction of sodium bisulfite; a method comprising addition of an amine compound (Japanese Patent Publication No. 31087/73) or addition of an amino acid such as glycine (Japanese Patent Publication No. 14/80) have been known.

However, in the distillation method, acrolein exhibits complicated behavior during purification. For example, during purification of acrylic acid, for example, the acrolein is readily dimerized into acrolein dimer during the distillation process as mentioned above or reacts with water to form $\beta$-hydroxylpropionaldehyde. On the other hand, large numbers of distillation plates and a large reflux ratio are required for the sufficient separation of aldehydes such as furfural and benzaldehyde because the difference in boiling point between these aldehydes and acrylic acid is small and because these aldehydes have small relative volatility against acrylic acid. It is disadvantageous from the industrial point of view to conduct rectification of polymerizable acrylic acid at a high temperature and under such severe conditions because special means and the like are required for preventing polymerization of the acid.

On the other hand, the adsorption method by means of activated carbon or the above mentioned molecular sieves requires a troublesome regeneration operation of the adsorbent used and, moreover, is unsatisfactory for the removal of trace amounts of impurities. The method comprising formation of sulfite addition products by the addition reaction of sodium bisulfite has almost no effectiveness in the case of purification of, for example, a 1,2-unsaturated carboxylic acid.

The method comprising addition of an amine compound or an amino acid fails to satisfactorily remove aldehyde impurities. Moreover, it is generally known that amine compounds have a polymerization-promoting effect on 1,2-unsaturated carboxylic acids and their esters. Also, some amines such as anhydrous hydrazine are unstable and dangerous, which gives rise to problems of process operation and safety.

SUMMARY OF THE INVENTION

The present invention provides a process for removing aldehydes contained in a 1,2-unsaturated carboxylic acid and/or its ester almost completely by very simple treatment operations, whereby the above described problems are solved. In accordance with the present invention, there can be obtained efficiently, economically and in a high yield, a 1,2-unsaturated carboxylic acid or its ester of extremely high purity, which does not cause problems with respect to aldehyde impurities when it is used as a starting material for synthesis of high-molecular compounds.

More specifically, the present invention provides a process for purifying a 1,2-unsaturated carboxylic acid and/or its ester containing aldehyde impurities, which comprises treating the 1,2-unsaturated carboxylic acid and/or its ester with a compound containing at least one mercapto group in the molecule in the presence of an acid catalyst.

It will be apparent from the examples which will be shown hereinbelow that, according to the present process, a compound containing at least one mercapto group in its molecule reacts with aldehyde impurities very selectively under moderate conditions in the presence of an acid catalyst, while giving rise to almost no reactions, such as the Michael addition reaction, with 1,2-unsaturated carboxylic acids and/or their esters, which possess highly active double bonds and carbonyl groups and exist in large amounts. From the reaction products, there can be obtained readily and efficiently 1,2-unsaturated carboxylic acids and/or their esters of very high purity.

DETAILED DESCRIPTION OF THE INVENTION

1,2-Unsaturated compounds

The 1,2-unsaturated carboxylic acids containing aldehydes as impurities to be purified according to the process of the present invention are 1,2-unsaturated carboxylic acids having 3 to 6 carbon atoms, preferably 3 or 4 carbon atoms, such as, for example, acrylic acid and methacrylic acid.

In general, the 1,2-unsaturated carboxylic acids are obtained by subjecting the corresponding alkenes and/or alkenals, etc. to a vapor-phase catalytic oxidation (as disclosed in, for example, Japanese Laid-Open Patent Nos. 102536/80, 113730/80, 73014/81 and 45130/82 Specifications), followed by conventional purification processes, i.e., distillation, extraction or the like, to remove a major part of the by-products. The 1,2-unsaturated carboxylic acids thus obtained by such a conventional purification process contain considerably less than about 2 wt. %, normally less than about 1 wt. %, of aldehyde impurities.

As the 1,2-unsaturated carboxylic acid esters containing aldehyde impurities, those which have been produced by the esterification reaction of the above-mentioned 1,2-unsaturated carboxylic acids according to a conventional method can be used. Specific examples of the 1,2-unsaturated carboxylic acid esters include methyl acrylate, methyl methacrylate, ethyl acrylate, ethyl methacrylate, butyl acrylate, butyl methacrylate, isobutyl acrylate, isobutyl methacrylate, hexyl acrylate, hexyl methacrylate, octyl acrylate, octyl methacrylate, lauryl acrylate, lauryl methacrylate, glycidyl acrylate, glycidyl methacrylate, methyl cellosolve acrylate, methyl cellosolve methacrylate, ethyl cellosolve acrylate, ethyl cellosolve methacrylate, 2-hydroxylethyl acrylate, 2-hydroxylethyl methacrylate, 2-hydroxylpropyl acrylate, 2-hydroxylpropyl methacrylate, N,N'-dimethylaminoethyl acrylate, N,N'-dimethylaminoethyl methacrylate, methyl carbitol acrylate, and methyl carbitol methacrylate.

In the case where the aldehyde impurities contained in the above mentioned esters are to be removed, the process according to the present invention can be applied before or after the esterification reaction of the corresponding 1,2-unsaturated carboxylic acids. Moreover, the process can also be applied during the esterification reaction.

Mercapto compounds

Any compound containing at least one mercapto group in its molecule can be used in the present method as long as it dissolves in the 1,2-unsaturated carboxylic acid or its ester. Specific examples of such compounds include alkyl mercaptans such as methyl mercaptan, ethyl mercaptan, n-propyl mercaptan, n-butyl mercaptan, n-hexyl mercaptan, 2-ethyl-n-hexyl mercaptan, n-octyl mercaptan, n-dodecyl mercaptan, and n-cetyl mercaptan, stearyl mercaptan, particularly those having 1 to 18 carbon atoms, preferably 8 to 18 carbon atoms; cycloalkyl mercaptans such as cyclohexyl mercaptan, alkenyl or cycloalkenyl mercaptans such as allyl mercaptan and 4-mercaptocyclopentene; alkoxyl- or aryloxy-alkyl (or -cycloalkyl)mercaptans such as methoxymethyl mercaptan, ethoxyethyl mercaptan, 3-ethoxyl-n-propyl mercaptan, 4-ethoxy-n-butyl mercaptan, 3-ethoxy-2-ethyl-n-hexyl mercaptan, 2-methoxycyclohexyl mercaptan, phenoxymethyl mercaptan, 2-phenoxyethyl mercaptan, 3-phenoxy-n-propyl mercaptan, and 2-phenoxycyclohexyl mercaptan; aralkyl group-containing mercaptans such as benzyl mercaptan, 2-phenylethyl mercaptan, 3-phenyl-n-propyl mercaptan, 2-phenyl-n-butyl mercaptan, and 2-phenyl-n-hexyl mercaptan; aryl mercaptans such as phenyl mercaptan, tolyl mercaptan and naphthyl mercaptan; halogenated aryl mercaptans such as p-chlorophenyl mercaptan, p-bromophenyl mercaptan, p-fluorophenyl mercaptan, p-iodophenyl mercaptan, 2-chloronaphthyl mercaptan, and 2-bromonaphthyl mercaptan; alkoxy- or aryloxy-aryl mercaptans such as p-methoxyphenyl mercaptan, p-ethoxyphenol mercaptan, p-propoxyphenyl mercaptan, and p-phenoxyphenyl mercaptan; alkaryl group-containing mercaptans such as o-methylphenyl mercaptan, p-methylphenyl mercaptan, p-ethylphenyl mercaptan, p-n-propylphenyl mercaptan, o-n-propylphenyl mercaptan, o-n-butylphenyl mercaptan, p-n-dodecylphenyl mercaptan and p-(2-ethoxy-n-hexyl)phenyl mercaptan; dimercaptans such as dithioethane, 1,2-propanedithiol, 1,3-propanedithiol, 1,4-butanedithiol, diethylene glycol dimercaptan, and triethylene glycol dimercaptan, particularly those having 1 to 18 carbon atoms, preferably 8 to 18 carbon atoms; mercapto alcohols and halogen-substituted mercapto alcohols such as 2-mercaptoethanol, 1-mercapto-2-propanol, 1-thioglycerol, and 1-chloro-3-mercapto-2-propanol; thiocarboxylic acids such as thioacetic acid and thiobenzoic acid; mercapto-substituted carboxylic acids and their ester derivatives such as thioglycolic acid, mercaptopropionic acid, thiosalicyclic acid, ethyl thioglycolate, and 2-ethylhexyl thioglycolate; as well as furfuryl mercaptan, 2-mercaptobenzothiazole, and 2-mercaptobenzoimidazole.

Such compounds containing at least one mercapto group can be used alone or as a mixture thereof.

The mercapto group-containing compounds especially preferred for use in the present invention are alkyl mercaptans and dimercaptans such as those exemplified above since they are highly efficacious, and alkyl mercaptans are most preferable because of their availability. More particularly, alkyl mercaptans having a boiling point not lower than that of n-dodecyl mercaptan, viz. ca. 270° C., are preferable for stabilization of acrylic acid.

The amount of the mercapto group-containing compound to be added depends on the concentration of the aldehyde impurities contained in the crude 1,2-unsaturated carboxylic acid and/or its ester as well as on the desired extent of the removal thereof, and is generally from equimole to 10-fold mole, preferably 3 to 5-fold mole, of the total molar amount of the aldehyde impurities.

The unreacted mercapto compound used and the reaction products produced by the reaction with the mercapto compound and the aldehyde impurities can, if desired, be readily separated by distillation in the presence of a conventional polymerization inhibitor such as hydroquinone or hydroquinone monomethyl ether after the reaction treatment. Therefore, the mercapto compound used in the present invention should be selected from the compounds having a large difference in boiling point from and advantageously having a boiling point higher than that of the 1,2-unsaturated carboxylic acid or its ester to be stabilized.

Acid catalyst

Any acid catalyst can be used in the present invention provided that it can donate ordinary protons. Examples of such acid catalysts include (1) proton acids such as mineral acids such as hydrochloric acid, sulfuric acid, nitric acid, and phosphoric acid; organic acids such as acetic acid, oxalic acid, and malonic acid; p-toluenesulfonic acid; sulfonated cation exchange resins such as sulfonic acid group-introduced resins of styrene-divinylbenzene copolymers, crosslinked polystyrene, and phenol-formaldehyde resin; and (2) Lewis acids such as zinc chloride and aluminum chloride.

The 1,2-unsaturated carboxylic acids themselves may be used as such an acid catalyst. However, the 1,2-unsaturated carboxylic acids are not preferred as the catalyst from an economical viewpoint in the industrial production since they are generally weak acids, and thus the reaction rate is decreased. It is preferable to use as the acid catalyst strong acids such as the above mentioned mineral acids, p-toluenesulfonic acid, and the sulfonated cation-exchange resins. Of these strong acids, the sulfonated cation-exchange resins are particularly preferred for the reasons that these resins not only provide the required acidity but also have low corrosive action on the apparatus used. Further, such solid acids as cation-exchange resins are preferable because they can be used in the form of a fixed bed through which a 1,2-unsaturated carboxylic acids and/or esters thereof are passed.

Stabilization

The process according to the present invention comprises treatment of a 1,2-unsaturated carboxylic acid and/or an ester thereof containing aldehyde impurities with a compound containing at least one mercapto group in the molecule in the presence of an acid catalyst. Such treatment can be carried out either in a batchwise system or in a continuous system. In one of the preferred embodiments of the process according to the invention, a particulate solid catalyst such as the sulfonated cation-exchange resins is used as the catalyst and the reaction is carried out by causing the reactants to flow through a fixed bed of the particulate catalyst.

The reaction temperature is in the range of 20° to 120° C., preferably 25° to 90° C. The reaction pressure is not especially restricted, a pressure sufficient for maintaining the liquid phase being satisfactory. It is advantageous, however, to employ a pressure in the range of 1 to 50 atm, preferably 1 to 5 atm. The reaction time depends upon the reaction conditions such as the type of the catalyst used, reaction temperature, and the reaction system but is ordinarily in the range of 0.1 to 24 hours, preferably 0.1 to 3 hours.

EXPERIMENTAL EXAMPLES

Examples 1 through 19

In an Erlenmeyer flask was placed 160 g of crude acrylic acid (acrylic acid: 99.7%, furfural: 250 ppm, benzaldehyde 190 ppm) which had been obtained through vapor-phase catalytic oxidation reaction of propylene followed by removal of water from the resulting aqueous solution of crude acrylic acid. The content of the flask was heated to the reaction temperature shown in Table 1, the specific amounts of the acid catalyst and the mercapto group-containing compound both shown in Table 1 were added thereto, and reaction was carried out under stirring for the reaction time given in Table 1.

The reaction products were analyzed by gas chromatography. The concentrations of furfural and benzaldehyde contained therein are shown in Table 1.

"SK-104" and "SK-102" in Table 1 refer to "Diaion SK-104" and "Diaion SK-102" (trade names of sulfonated cation-exchange resins supplied from Mitsubishi Chemical Industries Co., Ltd., Japan), respectively, which have been ion-exchanged to H-type resins, after which water has been removed in advance. Each resin was used in an amount of 7.5 g. The $H_2SO_4$ in the table is a guaranteed reagent (97%) and was used in an amount of 3.5 g.

TABLE 1

| Example No. | Mercapto compound | Acid catalyst | Reaction temperature (°C.) | Mercapto compd/aldehyde* (molar ratio) | Reaction time (hour) | Furfural (wt ppm) | Benzaldehyde (wt ppm) |
|---|---|---|---|---|---|---|---|
| 1 | n-butyl mercaptan | SK-104 | 70 | 7 | 0.5 | 5 | 19 |
| 2 | n-octyl mercaptan | SK-104 | 90 | 7 | 1 | 33 | 78 |
| 3 | n-dodecyl mercaptan | SK-104 | 90 | 7 | 1 | 43 | 87 |
| 4 | n-dodecyl mercaptan | $H_2SO_4$ | 60 | 7 | 0.5 | 3 | 92 |
| 5 | n-dodecyl mercaptan | none | 60 | 7 | 0.5 | 203 | 155 |
| 6 | n-dodecyl mercaptan | none | 60 | 7 | 4 | 107 | 128 |
| 7 | n-cetyl mercaptan | SK-104 | 70 | 7 | 0.5 | 10 | 20 |
| 8 | 1,2-ethanedithiol | SK-104 | 90 | 6 | 0.5 | Tr.** | Tr. |
| 9 | 1,4-butanedithiol | SK-104 | 70 | 7 | 0.5 | Tr. | Tr. |
| 10 | di(2-mercaptoethyl)ether | SK-104 | 90 | 8 | 0.5 | Tr. | Tr. |
| 11 | di(2-mercaptoethyl)ether | SK-104 | 70 | 8 | 0.5 | Tr. | Tr. |
| 12 | di(2-mercaptoethyl)ether | none | 70 | 8 | 0.5 | 228 | 178 |
| 13 | di(2-mercaptoethyl)ether | none | 70 | 8 | 4 | 150 | 161 |
| 14 | 2-mercaptoethanol | SK-104 | 90 | 8 | 2 | 13 | 38 |
| 15 | 1-thioglycerol | SK-102 | 90 | 7 | 0.5 | 18 | 17 |
| 16 | thioglycolic acid | SK-104 | 70 | 10 | 2.3 | 20 | 89 |
| 17 | 3-mercaptopropionic acid | SK-104 | 70 | 10 | 1.5 | 15 | 50 |
| 18 | thioacetic acid | SK-104 | 90 | 6 | 2 | 150 | 125 |
| 19 | 2-mercaptobenzothiazole | $H_2SO_4$ | 50 | 10 | 1.5 | 198 | 162 |

*aldehyde = furfural + benzaldehyde
**"Tr." means an amount not more than 1 ppm by weight.

Examples 20 through 22

In an Erlenmeyer flask was placed 100 g of crude methacrylic acid (methacrylic acid: 99.8%, furfural: 298 ppm, benzaldehyde: 222 ppm) which had been obtained through vapor-phase catalytic oxidation reaction of isobutylene followed by removal of water from the resulting aqueous solution of crude methacrylic acid. The content of the flask was heated to the reaction temperature shown in Table 2. Thereto were added 5 g of Diaion SK-104 (trade name, a sulfonated cation-exchange resin supplied from Mitsubishi Chemical Industries Co., Ltd., Japan) which had been ion-exchanged to H-type resin, and from which water had been removed in advance, and the mercapto compound shown in Table 2 in a 5-fold molar amount of the total molar amount of the furfural and benzaldehyde contained in the crude methacrylic acid, respectively. The mixture was then subjected to reaction under stirring for 1 hour.

The resulting products were analyzed by gas chromatography, the results of which are shown in Table 2.

TABLE 2

| Example No. | Mercapto compound | Reaction temperature (°C.) | Furfural (wt ppm) | Benzaldehyde (wt ppm) |
|---|---|---|---|---|
| 20 | n-dodecyl mercaptan | 50 | 45 | 90 |
| 21 | 1-thioglycerol | 90 | 20 | 25 |
| 22 | di(2-mercaptoethyl)ether | 90 | Tr. | Tr. |

Examples 23 through 43

A long glass tube (about 2.3 cm in inner diameter, about 50 cm in length and about 200 ml in internal volume) was charged with approximately 200 ml of Diaion PK 216 (trade name of a sulfonated cation-exchange resin supplied from Mitsubishi Chemical Industries Co., Ltd., Japan). A mixture of the crude acrylic acid as used in Examples 1 through 19 and n-dodecyl mercaptan added to the acrylic acid in the molar ratio shown in Table 3 was passed through the glass tube in an up-flow manner and subjected to continuous reaction at the reaction temperature and for the residence time shown in Table 3.

After completion of the reaction, the reaction products obtained from the top of the reaction tube were analyzed by gas chromatography. The results are shown in Table 3.

One liter each of the reaction products of Examples 37 and 43 was placed in a four-necked flask, respectively, and 1,000 ppm of hydroquinone and 500 ppm of hydroquinone monomethyl ether were added thereto as polymerization inhibitors. The content of the flask was subjected to simple distillation at 70° C. under 46 mmHg. About 900 cc of the distillate was taken from the top of the distillation column and analyzed by gas chromatography. Only trace amounts of furfural, benzaldehyde, unreacted n-dodecyl mercaptan and the polymerization products thereof were observed. It is apparent from the results that high-purity acrylic acid can be readily obtained by the above described process.

TABLE 3

| Example No. | Reaction temp. (°C.) | Residence time (hr.) | n-dodecyl mercaptan/aldehyde (molar ratio) | Furfural (wt ppm) | Benzaldehyde (wt ppm) |
|---|---|---|---|---|---|
| 23 | 50 | 0.8 | 5.0 | Tr.* | 3 |
| 24 | 40 | 3.0 | 5.0 | 11 | 21 |
| 25 | 40 | 2.0 | 5.0 | 11 | 15 |
| 26 | 40 | 1.0 | 5.0 | Tr. | 1 |
| 27 | 40 | 0.80 | 5.0 | Tr. | Tr. |
| 28 | 40 | 0.66 | 5.0 | Tr. | Tr. |
| 29 | 40 | 0.50 | 6.0 | Tr. | Tr. |
| 30 | 40 | 0.50 | 5.0 | Tr. | Tr. |
| 31 | 40 | 0.50 | 4.5 | Tr. | 1 |
| 32 | 40 | 0.50 | 3.0 | Tr. | 9 |
| 33 | 40 | 0.50 | 2.0 | 34 | 57 |
| 34 | 40 | 0.33 | 5.0 | Tr. | Tr. |
| 35 | 35 | 5.0 | 5.0 | Tr. | 1 |
| 36 | 30 | 5.0 | 5.0 | Tr. | Tr. |
| 37 | 30 | 2.0 | 5.0 | Tr. | Tr. |
| 38 | 30 | 1.0 | 5.0 | Tr. | Tr. |
| 39 | 30 | 0.5 | 5.0 | Tr. | Tr. |
| 40 | 25 | 5.0 | 5.0 | Tr. | Tr. |
| 41 | 25 | 2.0 | 5.0 | Tr. | Tr. |
| 42 | 25 | 1.0 | 5.0 | Tr. | Tr. |
| 43 | 25 | 0.5 | 5.0 | Tr. | Tr. |

*Tr.: trace

Example 44

A long glass tube (about 0.93 cm in inner diameter, about 50 cm in length and about 34 ml in internal volume) was charged with approximately 30 ml of Amberlist 15 (trade name of a sulfonated cation-exchange resin supplied from Rohm & Haas Company). Then, a mixture of the crude methacrylic acid as used in Examples 20 through 22 and n-dodecyl mercaptan added to the methacrylic acid in a 10-fold molar amount of the total molar amount of the furfural and benzaldehyde contained in the crude methacrylic acid was passed through the glass tube and subjected to continuous reaction at 50° C. with a residence time of 30 minutes.

After the reaction, the treated liquid was analyzed by gas chromatography whereupon only a trace amount each of furfural and benzaldehyde were found.

Example 45

To 100 g of the crude acrylic acid as used in Examples 1 through 19 were added 105 g of n-butanol, 100 g of benzene, 3 g of p-toluenesulfonic acid (PTSA), n-dodecyl mercaptan in an amount of 10 times the total molar amount of the furfural and benzaldehyde contained in the crude acrylic acid, and 0.2 g of hydroquinone. The resulting mixture was placed in a 500 ml three-necked flask and subjected to esterification at 90° C. for about 5 hours while dehydration was conducted.

After the reaction, unreacted acid and p-toluenesulfonic acid were neutralized. The resulting aqueous layer was separated, and then 0.2 g of additional hydroquinone was added to the reaction system. Then, benzene and unreacted n-butanol were distilled away under reduced pressure to obtain 82 g of n-butyl acrylate.

The n-butyl acrylate was analyzed by gas chromatography whereupon only a trace amount each of furfural and benzaldehyde were found.

Comparative Example 1

The esterification reaction shown in Example 45 was repeated except that no n-dodecyl mercaptan was added to produce 85 g of n-butyl acrylate.

The resulting n-butyl acrylate was analyzed as in Example 45. It was found that 85 ppm of furfural and 52 ppm of benzaldehyde were contained therein.

Example 46

Into butyl acrylate (99.61 wt % in purity) containing 95 ppm of furfural, 61 ppm of benzaldehyde and 21 ppm of acrolein dimer was added n-dodecyl mercaptan in an amount of 10 times the total molar amount of the above-mentioned aldehydes. The resulting mixture was subjected to continuous flow reaction at 40° C. with a residence time of 30 minutes by using the same reaction tube and catalyst as those used in Example 44. Only a trace amount each of furfural, benzaldehyde and acrolein dimer was found in the reaction products.

What is claimed is:

1. A process for purifying a 1,2-unsaturated carboxylic acid and or esters thereof selected from the group consisting of alkenoic acids having 3 to 6 carbon atoms and esters thereof, which 1,2-unsaturated carboxylic acid and or esters thereof contains aldehyde impurities, which comprises treating the alkenoic acid and/or the ester with a mercaptan compound at a temperature of 20°-120° C. in the presence of an acid catalyst.

2. The process according to claim 1, in which the 1,2-alkenoic acid is selected from the group consisting of acrylic acid and methacrylic acid.

3. The process according to claim 1, in which the acid catalyst is selected from the group consisting of a mineral acid, p-toluenesulfonic acid and a sulfonated cation-exchange resin.

4. The process as claimed in claim 1, in which the mercaptan compound is selected from the group consisting of alkyl mercaptan and dimercaptans, both of 1 to 18 carbon atoms.

5. The process as claimed in claim 1, in which the 1,2-unsaturated carboxylic acid is acrylic acid and the mercaptan compound is an alkylmercaptan having a boiling temperature not lower than approximately 270° C.

6. The process as claimed in claim 1, in which the mercaptan is an alkyl mercaptan having a boiling point of at least about 270° C.

7. The process as claimed in claim 6 in which the 1,2-alkenoic acid and/or ester is treated with the mercaptan compound in an amount of from equimole to 10 fold moles of the total molar amount of the aldehyde impurities.

8. The process as claimed in claim 1, in which the 1,2-alkenoic acid and/or ester is treated with the mercaptan compound in an amount of from equimole to 3 to 5 fold moles of the total molar amount of the aldehyde impurities.

9. The process as claimed in claim 1, in which the 1,2-alkenoic unsaturated acid and/or ester is treated with the mercaptan compound at a temperature of 25° to 90° C.

* * * * *